US00PP08595P

United States Patent [19]

Warriner, deceased

[11] Patent Number: Plant 8,595

[45] Date of Patent: Feb. 15, 1994

[54] HYBRID TEA ROSE PLANT NAMED 'JACCHRY'

[75] Inventor: William A. Warriner, deceased, late of Tustin, Calif., by Alene B. Warriner, legal representative

[73] Assignee: Bear Creek Gardens, Inc., Medford, Oreg.

[21] Appl. No.: 953,723

[22] Filed: Sep. 28, 1992

[51] Int. Cl.[5] ..... A01H 5/00

[52] U.S. Cl. ..... Plt./19

[58] Field of Search ..... Plt. 11, 19, 20

*Primary Examiner*—Howard J. Locker

*Attorney, Agent, or Firm*—Klarquist, Sparkman, Campbell, Leigh and Whinston

[57] ABSTRACT

Hybrid tea rose plant having distinctive large, well shaped flowers, strong stable deep pink flower color, vigorous upright growth habit, dark green glossy foliage and sweet smelling fragrance.

1 Drawing Sheet

The present invention relates to a new and distinct variety of rose plant of the hybrid tea class which was originated by the inventor by crossing an unnamed seedling with the variety Chrysler Imperial, U.S. Plant Pat. No. 1,167.

The primary objective of this breeding was to produce a new rose variety having the large glossy foliage of the female white flowered parent combined with the very large flower size and fragrance of the male parent. The objective was substantially achieved along with other desirable improvements as evidenced by the following unique combination of characteristics which are outstanding in the new variety and which distinguish it from its parents, as well as from all other varieties of which I am aware:

1. Very large well shaped hybrid tea buds and flowers;
2. Vigorous, upright habit of growth;
3. Glossy, dark green foliage;
4. Pleasant, sweet fragrance;
5. Strong, stable, deep pink flower color.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Chrysler Imperial, U.S. Plant Pat. No. 1,167.

Classification:

*Botanical.*—*Rosa hybrida.*

*Commercial.*—Hybrid tea.

FLOWER

Observations made from specimens grown in a garden in Somis, Calif., from March through August, 1992.

Blooming habit: Recurrent.

Bud:

*Size.*—1¾ inches when the petals start to unfurl.

*Form.*—Long, pointed ovoid.

*Color.*—When sepals first divide, bud color is Red Group 50A. When half blown, the upper sides of the petals are Red Groups 50A; and the lower sides of the petals are Red Group 50B to C.

*Sepals.*—Color: Green Group 138B with reddish cast. Surface texture: Covered in fine hairs. There are three normally to heavily appendaged sepals. There are two unappendaged sepals with hairy edges.

*Receptacle.*—Color: Green Group 137D. Shape: Apple. Size: Large (½×½ inches). Surface: Smooth.

*Peduncle.*—Length: Medium (3½ inches). Surface: Smooth with some glands. Color: Medium green. Strength: Stiff, erect.

Bloom:

*Size.*—Very large. Average open size is 5 to 6 inches.

*Borne.*—Singly.

*Stems.*—Medium (16 to 18 inches).

*Form.*—When first open: High centered. Permanence: Retains its form to the end; outer petals curl back.

*Petalage.*—Number of petals under normal conditions: 30.

*Color.*—The upper side of the petals is Red Group 50A. The reverse side of the petals is Red Group 50B to C. The bases of the petals have a large yellow half moon (½×½ inch) at the point of attachment. The major color on the upper side is Red Group 50A.

*Variegations.*—None.

*Discoloration.*—The general tonality at the end of the first day: No change. At the end of the third day: Under very hot conditions and bright sun there is some fading on petal margins to Red Group 50B to C.

*Fragrance.*—Moderate.

Petals:

*Texture.*—Thick, leathery.

*Shape.*—Round.

*Form.*—Tips slightly recurved.

*Arrangement.*—Imbricated, with few petaloids in the center.

*Persistence.*—Drop off cleanly.

*Lastingness.*—On the plant: Fair (4 to 5 days). As a cut flower: Long (6 to 7 days).

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles.*—Color: Red.

*Stigmas.*—Color: Yellow.

Form: Bush.

Growth: Very vigorous, upright, branching.

Foliage:

*Number of leaflets on normal mid-stem leaves.*—5 or 7.

*Size.*—Large (6×4 inches).

*Quantity.*—Abundant.

*Color.*—New foliage: Reddish. Old foliage: Dark green, glossy.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish.

*Petiole underside.*—Smooth with occasional prickle.

*Stipules.*—Medium, serrated, bearded.

*Diseases resistance.*—Susceptible to mildew, but resistant to rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked slightly downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its large, well shaped flowers, its strong stable deep pink flower color, its vigorous upright growth habit, its dark green glossy foliage and its sweet smelling fragrance.

* * * * *

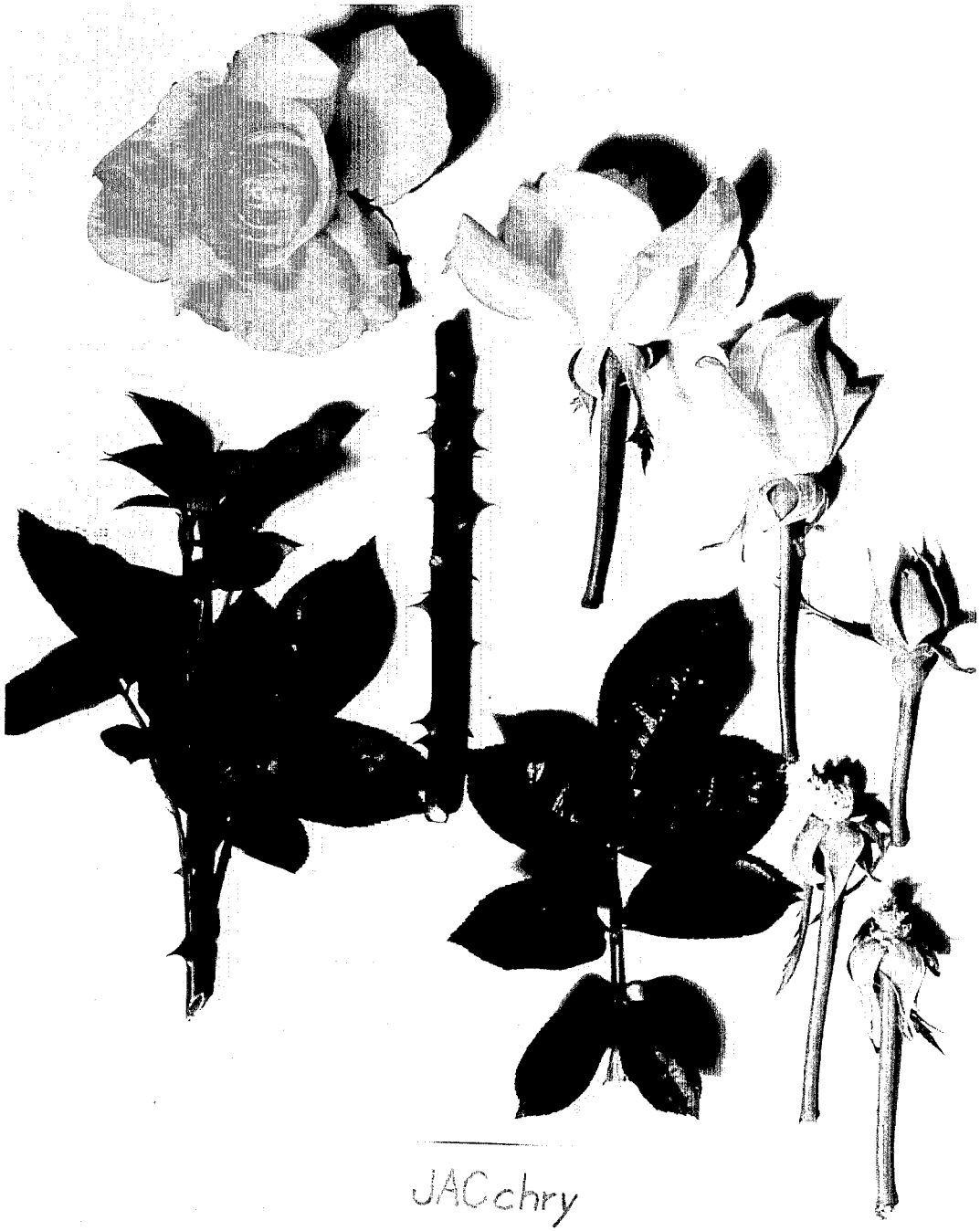
JACchry